United States Patent [19]
Bocek et al.

[11] Patent Number: 5,827,197
[45] Date of Patent: Oct. 27, 1998

[54] SYSTEM FOR DETECTING ATRIAL FIBRILLATION NOTWITHSTANDING HIGH AND VARIABLE VENTRICULAR RATES

[75] Inventors: Joseph M. Bocek, Seattle; David P. Finch, Bothell; Phillip D. Foshee, Jr., Woodinville; Jaeho Kim, Redmond, all of Wash.

[73] Assignee: InControl, Inc., Redmond, Wash.

[21] Appl. No.: 970,879

[22] Filed: Nov. 14, 1997

[51] Int. Cl.⁶ .................................................... A61N 1/39
[52] U.S. Cl. ............................................... 600/518; 607/5
[58] Field of Search ........................... 607/4, 5; 600/518

[56] References Cited

U.S. PATENT DOCUMENTS 5,522,852  6/1996  White et al. ................................. 607/5
5,562,709  10/1996  White ......................................... 607/5

*Primary Examiner*—Scott M. Getzow
*Attorney, Agent, or Firm*—Richard O. Gray, Jr.

[57] ABSTRACT

There is disclosed an implantable atrial defibrillator for applying cardioverting electrical energy to the atria of a heart when the atria are in need of cardioversion. The atrial defibrillator includes a sense channel adapted to be associated with at least one atrium of the heart to provide a cardiac signal during a plurality of cardiac cycles of the heart and a timer which determines a cardiac interval duration for each of the cardiac cycles. The defibrillator further includes an atrial detector for analyzing the cardiac signal provided by the sense channel during selected ones of the cardiac cycles wherein each one of the selected ones of the cardiac cycles has a cardiac interval greater than a predetermined duration.

A cardioverter applies cardioverting electrical energy to the atria responsive to the atrial detector detecting atrial fibrillation of the heart.

25 Claims, 1 Drawing Sheet

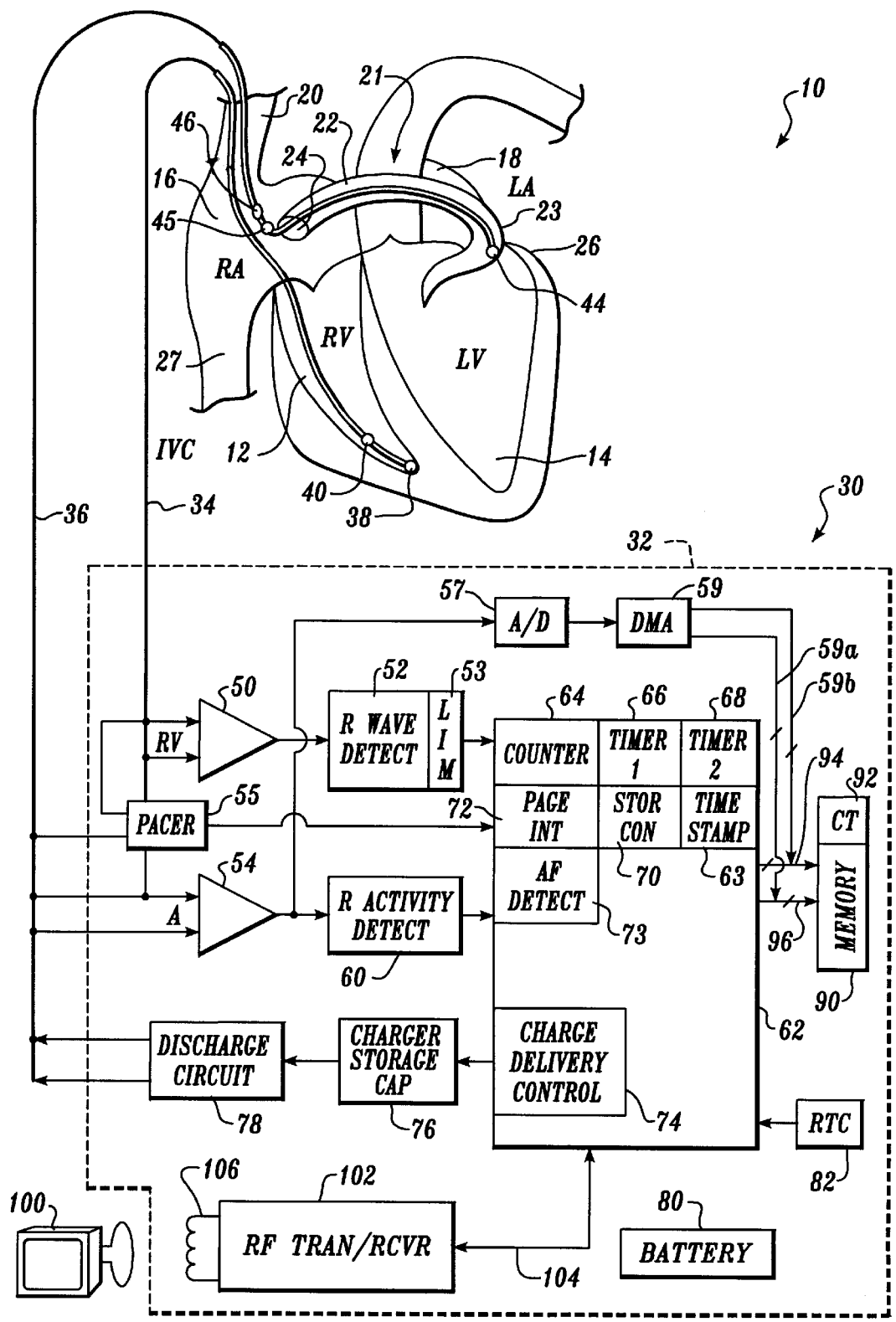

SYSTEM FOR DETECTING ATRIAL FIBRILLATION NOTWITHSTANDING HIGH AND VARIABLE VENTRICULAR RATES

BACKGROUND OF THE INVENTION

The present invention generally relates to an atrial defibrillator and method for applying cardioverting electrical energy to the atria of a human heart in need of cardioversion. The present invention is more particularly directed to an improved atrial fibrillation detection system for use in an implantable atrial defibrillator wherein cardiac activity detected in an atrial channel during selected cardiac cycles is analyzed for determining if the atria are in fibrillation. More specifically, the atrial fibrillation detection system and method of the present invention contemplates determining the duration of a cardiac interval associated with each cardiac cycle and analyzing only cardiac activity occurring in cardiac cycles having cardiac interval durations greater than a predetermined duration.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

The early implantable atrial defibrillators had been proposed to provide patients suffering from occurrences of atrial fibrillation with relief. Unfortunately, to the detriment of such patients, neither of these atrial defibrillators became a commercial reality. These defibrillators, although represented as being implantable, were not fully automatic, requiring human interaction for cardioverting or defibrillating the heart. Both of these proposed defibrillators required the patient to recognize the symptoms of atrial fibrillation. One defibrillator required a visit to a physician to activate the defibrillator and the other defibrillator required the patient to activate the defibrillator from external to the patient's skin with a magnet.

In order for an implantable atrial defibrillator to be truly automatic, it must include an atrial fibrillation detector which, responsive to monitored activity of the heart, determines if the atria are in fibrillation. To that end, atrial fibrillation detectors have been provided which analyze electrogram data of atrial activity which is collected during a preset data acquisition period and stored in memory. While such detectors have been successful, a problem can still arise in the quantity of good atrial electrogram data available for analysis. This can result because atrial electrogram data can be corrupted with other heart activity data, such as ventricular activity data. This is particularly the case if the electrogram data is derived from a vector susceptible to far field sensing of ventricular activity. Further, since atrial fibrillation causes ventricular rates to be high and variable, the amount of ventricular activity during a short cardiac cycle can greatly limit the amount of useful atrial activity data present during such short cardiac cycles. As a result, if atrial activity data is acquired during a data acquisition period of finite duration evidenced by numerous short cardiac cycles, the limited amount of available useful atrial activity data can adversely effect the accuracy in detecting atrial fibrillation.

SUMMARY OF THE INVENTION

The present invention provides a system for detecting an atrial arrhythmia of a heart. The system includes sensing means adapted to be associated with the atria of a heart for sensing electrical activity of the heart during at least one cardiac cycle of the heart to provide a cardiac signal and a detector for detecting a cardiac interval associated with the at least one cardiac cycle. The system further includes a timer for timing the duration of the cardiac interval and analyzing means for analyzing the cardiac signal to detect an atrial arrhythmia of the heart. The analyzing means analyzes the cardiac signal provided by the sensing means during the at least one cardiac cycle when the cardiac interval is greater in duration than a preselected duration.

The invention further provides a system for detecting an atrial arrhythmia including sensing means adapted to be associated with at least one atrium of a heart to provide a cardiac signal during a plurality of cardiac cycles of the heart, means for determining a cardiac interval duration for each of the cardiac cycles, and an atrial arrhythmia detector for analyzing the cardiac signal provided by the sensing means during selected ones of the cardiac cycles, each one of the selected ones of the cardiac cycles having a cardiac interval greater than a predetermined duration.

The invention further provides an implantable atrial defibrillator for applying cardioverting electrical energy to atria of a heart when the atria are in need of cardioversion. The atrial defibrillator includes sensing means adapted to be associated with the atria of a heart for sensing electrical activity of the heart during at least one cardiac cycle of the heart to provide a cardiac signal, a detector for detecting a cardiac interval associated with the at least one cardiac cycle, and a timer for timing the duration of the cardiac interval. The defibrillator further includes an atrial arrhythmia detector for analyzing the cardiac signal provided by the sensing means during the at least one cardiac cycle when the cardiac interval is greater in duration than a preselected duration to detect an atrial arrhythmia of the heart, and a cardioverter for applying cardioverting electrical energy to the atria responsive to the atrial arrhythmia detector detecting an atrial arrhythmia of the heart.

The invention still further provides an implantable atrial defibrillator for applying cardioverting electrical energy to atria of a heart when the atria are in need of cardioversion. The atrial defibrillator includes sensing means adapted to be associated with at least one atrium of a heart to provide a cardiac sigal during a plurality of cardiac cycles of the heart, means for determining a cardiac interval duration for each of the cardiac cycles, an atrial arrhythmia detector for analyzing the cardiac signal provided by the sensing means during selected ones of the cardiac cycles, each one of the selected ones of the cardiac cycles having a cardiac interval greater than a predetermined duration, and a cardioverter for applying cardioverting electrical energy to the atria responsive to the atrial arrhythmia detector detecting an atrial arrhythmia of the heart.

BRIEF DESCRIPTION OF THE DRAWINGS

The features of the present invention which are believed to be novel are set forth with particularity in the appended claims.

The invention, together with further objects and advantages thereof, may best be understood by making reference to the following description taken in conjunction with the accompanying drawing, in the sole FIGURE of which like reference numerals identify identical elements, and wherein the sole FIGURE is a schematic block diagram of a fully implantable atrial defibrillator embodying the present invention for applying defibrillating electrical energy to the atria of a human heart and which is shown in association with the human heart in need of atrial fibrillation monitoring and potential cardioversion of the atria.

DETAILED DESCRIPTION OF THE PREFERRED EMBODIMENT

Prior to referring to the sole FIGURE, a general description of a typical or normal cardiac cycle may be helpful in understanding the operation and various aspects of the present invention. The beginning of a cardiac cycle in normal sinus rhythm is initiated by a P wave which is normally a small positive wave. The P wave which may also be referred to as an A wave induces depolarization of the atria of the heart. Following the P wave there is a cardiac cycle portion which is substantially constant having a time duration on the order of, for example, 120 milliseconds.

The QRS complex of the cardiac cycle then normally occurs after the substantially constant portion. The dominating feature of the QRS complex is the R wave which is a rapid positive or negative deflection. The R wave generally has an amplitude greater than any other wave of the cardiac cycle and is characterized by a rapid deviation from and return toward baseline. The R wave is the depolarization of the ventricles and hence, as used herein, the term "ventricular activations" denotes R waves of the heart cardiac cycle. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds. While the P wave in actuality initiates each new cardiac cycle, cardiac cycles are generally timed based upon detected R to R intervals because R wave detection is generally thought to be most reliable given the extreme amplitude and spiked shape of the R waves. Hence, as used herein, the term "cardiac cycle" is meant to denote the activity of the heart during immediately succeeding R waves.

Referring now to the sole FIGURE, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in the sole FIGURE are the right ventricle 12, the left ventricle 14, the right atrium 16, and left atrium 18, the superior vena cava 20, the coronary sinus channel 21 which, as used herein, denotes the cronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an intravascular first lead 36, and an endocardial second lead 34. The enclosure 32 and first and second leads 36 and 34 are arranged to be implanted beneath the skin of a patient so as to render the atrial defibrillator 30 fully implantable.

The first lead 36 generally includes a first or tip electrode 44, a second or intermediate electrode 45, and a third or proximal electrode 46. As illustrated, the first lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44, 45, and 46 are spaced apart such that when the first electrode 44 is positioned as described above, the second electrode 46 is in the right atrium 16 and the second electrode 45 is within the right atrium 16 adjacent the coronary sinus ostium 24. The first electrode 44 together with the third electrode 46 provide bi-polar sensing of heart activity in the atria 16 and 18 and the third electrode 46 together with the second electrode 45 provide bi-polar sensing and pacing in the right atrium 16. Alternatively, electrodes 44 and 45 may be used for sensing atrial activity.

The first electrode 44 and the third electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. The electrodes 44 and 46 are preferably elongated cardioverting electrodes. The electrode 45 is preferably a small surface area pacing electrode of the type known in the art.

The second lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle and pacing in the right ventricle. As illustrated, the lead 34 is fed through the superior vena cava 20, into the right atrium 16, and then into the right ventricle 12.

Within the enclosure 32, the atrial defibrillator 30 includes a first sense amplifier 54, an atrial activity detector 60, a second sense amplifier 50, and an R wave detector 52. The first sense amplifier 54 forms a first sensing means which together with electrodes 44 and 46 of the first lead 36 to which sense amplifier 54 is coupled, senses cardiac activity of the heart in or near the atria 16 and 18 and provides a cardiac signal to the atrial activity detector 60. The sense amplifier 50 forms a second sensing means which, together with electrodes 38 and 40 of the second lead 34 to which it is coupled senses cardiac activity in the right ventricle of the heart to provide a second cardiac signal to the R wave detector 52. Preferably both the sense amplifier 54 and the sense amplifier 50 include a differentiating filter so that the first cardiac signal provided by sense amplifier 54 and the second cardiac signal provided by sense amplifier 50 are differentiated first and second cardiac signals respectively.

The R wave detector 52 provides one or more output pulses for each R wave sensed during a cardiac cycle of the heart. To that end, the R wave detector may include a further differentiating filter for differentiating the differentiated second cardiac signal provided by sense amplifier 50 resulting in a twice differentiated second cardiac signal. The R wave detector 52 may further include a threshold circuit for setting an upper and lower threshold which provides an output when the twice differentiated second cardiac signal transitions beyond either the upper or lower thresholds.

Finally, the R wave detector preferably further includes an output pulse rate limiter 53 having a programmable pulse repetition time interval. The pulse repetition time interval is set to be as short as possible to allow detection of the last threshold crossing for an R wave. The R wave detector 52 thus provides at least one such pulse to indicate the beginning of each detected R wave and one such pulse to indicate the completion of each detected R wave so that the beginning and end of each R wave may be determined.

The enclosure 32 of the atrial defibrillator 30 further includes a microprocessor 62. The microprocessor 62 is preferably implemented in accordance with this embodiment of the present invention to result in a plurality of functional stages. The stages include a time stamp stage 63, a counter stage 64, a first timer stage 66, a second timer stage 68, a third timer stage 69, a storage control stage 70, a pace interrupt stage 72, an atrial arrhythmia detector in the form of an atrial fibrillation detector 73 and a charge delivery and energy control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or for receiving programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from the external controller 100 and for transmitting data to the external controller 100. One preferred communication system is disclosed in copending U.S. Pat. No. 5,342,408 which issued on Aug. 30, 1994 for "Telemetry System for an Implantable Cardiac Device," which patent is assigned to the assignee of the present invention and incorporated herein by reference.

The atrial defibrillator 30 further includes a pacer 55 which is coupled to electrodes 38 and 40 of lead 34 and to electrodes 45 and 46 of lead 36. Alternatively, a separate lead commonly referred to a "J lead" having a pair of pacing electrodes may be employed. The pacer 55 preferably includes circuitry for sensing ventricular activity with electrodes 38 and 40 and pacing circuitry for applying pacing pulses to the ventricles with electrodes 38 and 40. Similarly, the pacer 55 preferably includes circuitry for sensing atrial activity with electrodes 45 and 46 and pacing circuitry for applying pacing pulses to the atria with electrodes 45 and 46. Further, the pacer 55 may utilize the ventricular and atrial sensing and pacing circuitry to provide single chamber pacing in either the right ventricle 12 or right atrium 16, asynchronously or on demand, or dual chamber pacing in a manner known in the art. The pacer is coupled to the pace interrupt stage 72 for providing an interrupt signal whenever a pacing pulse is supplied to either the right ventricle or the right atrium. The function of the interrupt signal will be described subsequently.

The atrial defibrillator 30 further includes an analog to digital converter 57 and a direct memory access controller (DMA) 59. The analog to digital converter 57 has an input coupled to the output of sense amplifier 54 for receiving the cardiac signal representing atrial activity of the heart sensed by electrodes 44 and 46. During data acquisition, the analog to digital converter 57 converts the cardiac signal into digital data. The digital data is received by the DMA 59 and conveys the digital data to memory 90 over a data bus 59a for storage in memory at predetermined locations selected by the DMA 59 over an address bus 59b. The cardiac signal thus stored in digital form representing atrial activity of the heart is thereafter utilized by the atrial fibrillation detector 73 for detecting the presence of atrial fibrillation of the heart.

To complete the identification of the various structural elements within the enclosure 32, the atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. Lastly, the defibrillator 30 includes a depletable power source 80, such as a lithium battery, for providing power to the electrical components of the atrial defibrillator 30, and a real time clock 82.

In accordance with a preferred embodiment of the present invention, a data acquisition is begun at spaced apart times by the third time 69 enabling the microprocessor 62 which in turn enables the sense amplifiers 50 and 54, the R wave detector 52, the atrial activity detector 60, the analog to digital converter 57, and the DMA 59. A data acquisition period is timed by the timer 66 under control of the storage control stage 70. The data acquisition period preferably has a duration long enough for spanning a plurality of cardiac cycles and, for example, eight seconds. During the eight second data acquisition period, the cardiac signal from sense amplifier 54 is digitized by the analog to digital converter 57 into digital data and the digital data is caused to be stored in the memory 90 by the DMA 59 as previously described. Also during this time, each output of the R wave detector 52 causes an interrupt to the microprocessor 62. Each R wave interrupt is time stamped by the time stamp stage 63. Each R wave interrupt time stamp is then stored in the memory 90 along with the digital data from DMA 59. Alternatively, each cardiac event may be stored in a data array (not shown) in which each entry corresponds to the presence or absence of an event within a given time slice, such as eight milliseconds or four milliseconds.

After the eight second data acquisition period is completed, the storage control stage 70 causes the second timer stage 68 to determine a cardiac interval for each cardiac cycle which occurred during the data acquisition period. The timer 68 utilized the R wave interrupt time stamps which denote the beginning of each cardiac cycle to identify each cardiac cycle. Alternatively, if the aforementioned data array is utilized, the data array is reviewed under software control to determine the R wave start and end points. The cardiac cycles may then be identified.

The timer 6B then determines, for each cardiac cycle for which data was stored, a cardiac interval chosen to assure that during the tenure thereof, the digital cardiac signal stored in memory 90 will be free of ventricular activity artifact and other artifact which may contaminate the desired atrial activity data required by the atrial fibrillation detector 73 in detecting atrial fibrillation. For example, the cardiac interval for each cardiac cycle may be chosen and identified by the timer 68 to commence at the end of each R wave and end at the beginning of the next immediately succeeding R wave. These times may be discerned by the timer stage 68 from the R wave time stamped interrupts to derive a cardiac interval duration for each cardiac cycle.

The storage control stage 70 then determines which ones of the cardiac cycles have cardiac intervals durations greater than a preselected duration. Those cardiac cycles having cardiac interval durations longer in duration than the preselected duration are identified by the storage control stage 70. The preselected cardiac interval duration is selected to assure that the atrial fibrillation detector 73 will eventually have sufficient stored atrial activity data to analyze for detecting atrial fibrillation and may be, for example, in the range of about four hundred (400) to seven hundred (700) milliseconds (ms).

As the storage control stage 70 identifies each cardiac cycle having a cardiac interval duration greater than the preselected duration, the counter stage 64 is incremented. When the cardiac interval durations of all the cardiac cycles from the data acquisition period have been determined and the cardiac cycles satisfying the cardiac interval duration criteria have been identified by the storage control 70, the storage control 70 then determines if sufficient data has been acquired. This may be accomplished by comparing the count in counter 64 to a preselected count previously stored in storage location 92 of memory 98. If the count in counter 64 is equal to or greater than the preselected count which may be, for example, four to sixteen inclusive, the storage control 70 then activates the atrial fibrillation detector 73. The atrial fibrillation detector 73 then preferably analyzes the stored cardiac digital data for only those cardiac cycles selected as satisfying the cardiac interval duration criteria and particularly, the data for each such selected cardiac cycle occurring within its respective cardiac cycle interval. In this way, the atrial fibrillation detector will be assured of having sufficient uncontaminated data to analyze.

If the counter in counter 64 is less than the preselected count, the storage control stage 70 will cause another data acquisition period to be started. After this acquisition period, the cardiac interval duration analysis procedure is repeated.

Alternatively, to conserve on memory space, the atrial fibrillation detector may analyze the data for each data segment which meets the criteria. Once analyzed, the current segment may be overwritten with new data. After each analysis, a check may be made to determine if enough cumulative data has been analyzed.

The determination of sufficient data may alternatively be based upon a total duration of the cardiac intervals of the cardiac cycles having cardiac intervals satisfying the cardiac interval criteria. An accumulated cardiac interval duration may be maintained in timer stage 68 or a further dedicated timer stage (not shown). Hence, when the accumulated or total cardiac interval duration exceeds a predetermined total duration, the storage control 70 will then activate the atrial fibrillation detector 73. The predetermined total duration may, for example, be between 5 and 12 seconds.

Data acquisition for atrial fibrillation detection, in accordance with a further aspect of the present invention, may be coordinated with pacing of the heart by pacer 55. Each time the pacer 55 paces the heart to cause a driven R wave, it provides a pace interrupt to the pace interrupt stage 72 which serves as a pacing pulse detector. The pace interrupts are time stamped by the time stamp stage 63. If during a data acquisition the pacer 55 issues a ventricular pacing pulse, the timer 68 will identify the cardiac interval duration as ending upon the pace interrupt time stamp resulting from the detection of the ventricular pacing pulse by the pace interrupt stage 72. It will also identify the cardiac interval of the next succeeding cardiac cycle as beginning with the ventricular pace interrupt time stamp plus a preset interval to account for the width of the driven R wave. If ventricular pacing is not required during a cardiac cycle, the cardiac intervals will be identified based upon a naturally occurring R wave as previously described.

If the atria are paced, the timer stage 68 will identify a cardiac interval as ending upon a pace interrupt time stamp resulting from the detection of an atrial pacing pulse by the pace interrupt stage 72. The cardiac interval of the next succeeding cardiac cycles will then be identified by the timer stage 68 as beginning upon a ventricular pacing pulse plus the preset interval to account for the width of the driven R wave or at the end of the next naturally occurring R wave. As a result, single chamber pacing or dual chamber pacing may be coordinated with atrial fibrillation data acquisition.

As a result of the foregoing, the present invention provides a means by which sufficient and uncontaminated data may be acquired for atrial fibrillation detection. This data acquisition may further be achieved even if the heart is paced in either a single chamber atrial or ventricular mode or a dual chamber mode.

In accordance with this preferred embodiment, when the data acquisition is completed, the storage control 70 enables the atrial fibrillation detector 73. As previously mentioned, the atrial fibrillation detector 73 preferably analyzes only the data occurring during the cardiac intervals of the selected cardiac cycles which satisfied the cardiac interval duration criteria. The atrial fibrillation detector 73 may determine if the atria 16 and 18 are in fibrillation in a manner known in the art as, for example, described in U.S. Pat. No. 5,486,199 which issued on Jan. 13, 1996 for "System and Method For Reducing False Positives In Atrial Fibrillation Detection," which patent is assigned to the assignee of the present invention and incorporated herein by reference. If the atria are in fibrillation and thus in need of cardioversion, the charge delivery control 74 causes the charger and storage capacitor circuit 76 to charge the storage capacitor within the circuit 76 to a selected peak voltage. Thereafter, and in timed relation to a detected or driven R wave, the discharge circuit 78, applies a portion of the stored electrical energy to electrodes 44 and 46 and thus the atria 16 and 18 to cardiovert the atria 16 and 18.

While a particular embodiment of the present invention has been shown and described, modifications may be made. For example, instead of determining the cardiac interval durations based upon pre-stored time stamps, the timer 68 may determine the cardiac interval durations in real time as the interrupts and time stamps occur. This is made possible because the DMA 59 functions independently of the microprocessor 62 during data acquisition. Also, the broader aspects of the present inventions are not intended to be limited to any particular atrial arrhythmia detection method. As will be appreciated by those skilled in the art, the present invention may be employed to advantage in any atrial arrhythmia detection system which analyzes atrial activity data. Hence, it is intended in the appended claims, to cover all such changes and modifications which may fall within the true spirit and scope of the invention.

What is claimed is:

1. A system for detecting an atrial arrhythmia of a heart, said system comprising:

sensing means adapted to be associated with the atria of a heart for sensing electrical activity of the heart during at least one cardiac cycle of the heart and providing a cardiac signal;

a detector for detecting a cardiac interval associated with the at least one cardiac cycle;

a timer for timing the duration of the cardiac interval; and analyzing means for analyzing the cardiac signal to detect the atrial arrhythmia of the heart, the analyzing means analyzing the cardiac signal provided by the sensing means during the at least one cardiac cycle when the cardiac interval is greater in duration than a preselected duration.

2. A system for detecting an atrial arrhythmia comprising:

sensing means adapted to be associated with at least one atrium of a heart to provide a cardiac signal during a plurality of cardiac cycles of the heart;

means for determining a cardiac interval duration for each of the cardiac cycles; and an atrial arrhythmia detector for analyzing the cardiac signal provided by the sensing means during selected ones of the cardiac cycles, each one of the selected ones of the cardiac cycles having a cardiac interval greater than a predetermined duration.

3. A system as defined in claim 2 further including a counter for counting the cardiac cycles having cardiac intervals greater than said predetermined duration and wherein said atrial arrhythmia detector is responsive to the counter reaching a preselected count for commencing analysis of the cardiac signal.

4. A system as defined in claim 3 wherein said preselected count is four to and including sixteen.

5. A system as defined in claim 2 further including an R wave detector for detecting each R wave of the heart and wherein a current cardiac interval ends and an immediately successive cardiac interval begins with each detected R wave.

6. A system as defined in claim 5 further including means for detecting the beginning and end of each R wave and wherein each cardiac interval begins at the end of each R wave and ends at the beginning of each immediately successive R wave.

7. A system as defined in claim 2 further including pacing pulse detecting means for detecting an occurrence of a ventricular pacing pulse being applied to the heart and wherein a current cardiac interval ends upon detection of a pacing pulse and an immediately successive cardiac interval begins a preset time after detection of a ventricular pacing pulse.

8. A system as defined in claims 2 further including pacing pulse detecting means for detecting an occurrence of an atrial pacing pulse being applied to the heart and wherein a current cardiac interval ends upon detection of an atrial pacing pulse by the pacing pulse detecting means.

9. A system as defined in claim 2 further including a timer for timing a total duration of the cardiac intervals of the selected ones of the cardiac cycles, and wherein the atrial fibrillation detector is responsive to the total duration reaching a predetermined total duration for analyzing the selected ones of the cardiac cycles.

10. A system as defined in claim 2 further including a memory for storing the cardiac signal and wherein the atrial fibrillation detector is coupled to the memory for analyzing the cardiac signal stored during the selected cardiac cycles.

11. A system as defined in claim 10 further including a storage control for causing the cardiac signal to be stored in the memory during at least one storage period of finite duration.

12. A system as defined in claim 10 further including a storage control for causing the cardiac signal to be stored in the memory during storage periods of fixed duration and for reinitiating a storage period until a given quantity of selected cardiac cycles have been stored.

13. An implantable atrial defibrillator for applying cardioverting electrical energy to atria of a heart when the atria are in need of cardioversion, the atrial defibrillator comprising:

sensing means adapted to be associated with the atria of a heart for sensing electrical activity of the heart during at least one cardiac cycle of the heart and providing a cardiac signal;

a detector for detecting a cardiac interval associated with the at least one cardiac cycle;

a timer for timing the duration of the cardiac interval;

an atrial arrhythmia detector for analyzing the cardiac signal provided by the sensing means during the at least one cardiac cycle when the cardiac interval is greater in duration than a preselected duration to detect an atrial arrhythmia of the heart; and a cardioverter for applying cardioverting electrical energy to the atria responsive to the atrial arrhythmia detector detecting an atrial arrhythmia of the heart.

14. An implantable atrial defibrillator for applying cardioverting electrical energy to atria of a heart when the atria are in need of cardioversion, the atrial defibrillator comprising:

sensing means adapted to be associated with at least one atrium of a heart to provide a cardiac signal during a plurality of cardiac cycles of the heart;

means for determining a cardiac interval duration for each of the cardiac cycles;

an atrial arrhythmia detector for analyzing the cardiac signal provided by the sensing means during selected ones of the cardiac cycles, each one of the selected ones of the cardiac cycles having a cardiac interval greater than a predetermined duration; and a cardioverter for applying cardioverting electrical energy to the atria responsive to the atrial arrhythmia detector detecting an atrial arrhythmia of the heart.

15. An atrial defibrillator as defined in claim 14 further including a counter for counting the cardiac cycles having cardiac intervals greater than said predetermined duration and wherein said atrial arrhythmia detector is responsive to the counter reaching a preselected count for commencing analysis of the cardiac signal.

16. An atrial defibrillator as defined in claim 15 wherein said preselected count is four to an including sixteen.

17. An atrial defibrillator as defined in claim 14 further including an R wave detector for detecting each R wave of the heart and wherein a current cardiac interval ends and an immediately successive cardiac interval begins with each detected R wave.

18. An atrial defibrillator as defined in claim 17 further including means for detecting the beginning and end of each R wave and wherein each cardiac interval begins at the end of each R wave and ends at the beginning of each immediately successive R wave.

19. An atrial defibrillator as defined in claim 14 further including pacing means for applying pacing pulses to the heart and pacing pulse detecting means for detecting an occurrence of a ventricular pacing pulse being applied to the heart and wherein a current cardiac interval ends upon detection of a pacing pulse and an immediately successive cardiac interval begins a preset time after detection of a ventricular pacing pulse.

20. An atrial defibrillator as defined in claim 14 further including pacing means for applying pacing pulses to the heart and pacing pulse detecting means for detecting an occurrence of an atrial pacing pulse being applied to the heart and wherein a current cardiac interval ends upon detection of an atrial pacing pulse by the pacing pulse detecting means.

21. An atrial defibrillator as defined in claim 20 wherein the pacing means is a dual chamber pacer.

22. An atrial defibrillator as defined in claim 14 further including a timer for timing a total duration of the cardiac intervals of the selected ones of the cardiac cycles, and wherein the atrial fibrillation detector is responsive to the total duration reaching a predetermined total duration for analyzing the selected ones of the cardiac cycles.

23. An atrial defibrillator as defined in claim 14 further including a memory for storing the cardiac signal and wherein the atrial fibrillation detector is coupled to the memory for analyzing the cardiac signal stored during the selected ones of cardiac cycles.

24. An atrial defibrillator as defined in claim 23 further including a storage control for causing the cardiac signal to be stored in the memory during at least one storage period of finite duration.

25. An atrial defibrillator as defined in claim 23 further including a storage control for causing the cardiac signal to be stored in the memory during storage periods of fixed duration and for reinitiating a storage period until a given quantity of selected cardiac cycles have been stored.

\* \* \* \* \*